(12) United States Patent
Jacobsen et al.

(10) Patent No.: US 12,193,783 B2
(45) Date of Patent: *Jan. 14, 2025

(54) NAVIGATION AND LOCAL THERMOMETRY

(71) Applicant: Medtronic Navigation, Inc., Louisville, CO (US)

(72) Inventors: Brad Jacobsen, Erie, CO (US); Andrew Bzostek, Boulder, CO (US); Daniel Dunford, Broomfield, CO (US); Benjamin D. Ewing, Westminster, CO (US); Amir Ghanei, Arvada, CO (US); Bryan Wilson, Broomfield, CO (US); Janine Benavente, Madrid (ES)

(73) Assignee: Medtronic Navigation, Inc., Lafayette, CO (US)

( * ) Notice: Subject to any disclaimer, the term of this patent is extended or adjusted under 35 U.S.C. 154(b) by 429 days.

This patent is subject to a terminal disclaimer.

(21) Appl. No.: 17/453,913

(22) Filed: Nov. 8, 2021

(65) Prior Publication Data

US 2022/0125313 A1 Apr. 28, 2022

Related U.S. Application Data

(63) Continuation of application No. 15/141,282, filed on Apr. 28, 2016, now Pat. No. 11,172,821.

(51) Int. Cl.
*A61B 5/00* (2006.01)
*A61B 5/01* (2006.01)
(Continued)

(52) U.S. Cl.
CPC .............. *A61B 5/0036* (2018.08); *A61B 5/01* (2013.01); *A61B 5/015* (2013.01); *A61B 5/062* (2013.01);
(Continued)

(58) Field of Classification Search
CPC ......... A61B 5/01; A61B 5/062; A61B 5/0036; A61B 5/015; A61B 5/065; A61B 5/743;
(Continued)

(56) References Cited

U.S. PATENT DOCUMENTS 4,140,130 A 2/1979 Storm, III
4,362,161 A 12/1982 Reimels et al.
(Continued)

FOREIGN PATENT DOCUMENTS

CA 2548226 A1 5/2005
CN 1511011 A 7/2004
(Continued)

OTHER PUBLICATIONS

Office Action regarding Korean Patent Application No. 10-2018-7034420, dated Dec. 3, 2021. .
(Continued)

*Primary Examiner* — Chao Sheng
(74) *Attorney, Agent, or Firm* — Harness, Dickey & Pierce, P.L.C.

(57) ABSTRACT

A system including a thermal sensor with an instrument placed in a volume. The thermal sensor may be useful in determining a temperature at a surface of the instrument and a distance away from the instrument. A therapy may be performed based on a sensed temperature with the thermal sensors.

16 Claims, 5 Drawing Sheets

(51) Int. Cl.
*A61B 5/06* (2006.01)
*A61B 8/00* (2006.01)
*A61B 18/22* (2006.01)
*A61N 5/06* (2006.01)
*A61N 5/067* (2006.01)
*A61B 34/20* (2016.01)
*A61B 90/00* (2016.01)

(52) U.S. Cl.
CPC .............. *A61B 5/065* (2013.01); *A61B 5/743* (2013.01); *A61B 5/7435* (2013.01); *A61B 5/748* (2013.01); *A61B 8/00* (2013.01); *A61B 18/22* (2013.01); *A61N 5/0601* (2013.01); *A61N 5/0625* (2013.01); *A61B 2034/2046* (2016.02); *A61B 2090/374* (2016.02); *A61B 2090/376* (2016.02); *A61N 2005/0612* (2013.01); *A61N 2005/0627* (2013.01); *A61N 5/067* (2021.08)

(58) Field of Classification Search
CPC ......... A61B 5/7435; A61B 5/748; A61B 8/00; A61B 18/22; A61B 2034/2046; A61B 2090/374; A61B 2090/376; A61N 5/0601; A61N 5/0625; A61N 5/067; A61N 2005/0612; A61N 2005/0627
See application file for complete search history.

(56) References Cited

U.S. PATENT DOCUMENTS

| | | |
|---|---|---|
| 4,466,697 A | 8/1984 | Daniel |
| 4,515,165 A | 5/1985 | Carroll |
| 4,554,925 A | 11/1985 | Young |
| 4,580,561 A | 4/1986 | Williamson |
| 4,585,298 A | 4/1986 | Mori |
| 4,608,977 A | 9/1986 | Brown |
| 4,633,875 A | 1/1987 | Turner |
| 4,638,800 A | 1/1987 | Michel |
| 4,641,650 A | 2/1987 | Mok |
| 4,660,952 A | 4/1987 | Toyoda et al. |
| 4,669,467 A | 6/1987 | Willett et al. |
| 4,693,556 A | 9/1987 | McCaughan, Jr. |
| 4,740,047 A | 4/1988 | Abe et al. |
| 4,785,815 A | 11/1988 | Cohen |
| 4,832,024 A | 5/1989 | Boussignac et al. |
| 4,852,567 A | 8/1989 | Sinofsky |
| 4,862,887 A | 9/1989 | Weber et al. |
| 4,923,459 A | 5/1990 | Nambu |
| 4,959,063 A | 9/1990 | Kojima |
| 4,960,109 A | 10/1990 | Lele |
| 4,986,628 A | 1/1991 | Lozhenko et al. |
| 5,042,980 A | 8/1991 | Baker et al. |
| 5,050,597 A | 9/1991 | Daikuzono |
| 5,061,265 A | 10/1991 | Abela et al. |
| 5,074,632 A | 12/1991 | Potter |
| 5,116,345 A | 5/1992 | Jewell et al. |
| 5,151,096 A | 9/1992 | Khoury |
| 5,169,396 A | 12/1992 | Dowlatshahi et al. |
| 5,196,005 A | 3/1993 | Doiron et al. |
| 5,207,669 A | 5/1993 | Baker et al. |
| 5,219,346 A | 6/1993 | Wagnieres et al. |
| 5,222,953 A | 6/1993 | Dowlatshahi |
| 5,246,436 A | 9/1993 | Rowe |
| 5,269,777 A | 12/1993 | Doiron et al. |
| 5,281,232 A | 1/1994 | Hamilton et al. |
| 5,292,320 A | 3/1994 | Brown et al. |
| 5,303,324 A | 4/1994 | Lundahl |
| 5,307,812 A | 5/1994 | Hardy et al. |
| 5,312,392 A | 5/1994 | Hofstetter et al. |
| 5,323,779 A | 6/1994 | Hardy et al. |
| 5,327,884 A | 7/1994 | Hardy et al. |
| 5,330,465 A | 7/1994 | Doiron et al. |
| 5,334,191 A | 8/1994 | Poppas et al. |
| 5,337,381 A | 8/1994 | Biswas et al. |
| 5,342,357 A | 8/1994 | Nardella |
| 5,348,552 A | 9/1994 | Nakajima et al. |
| 5,363,458 A | 11/1994 | Pan et al. |
| 5,368,031 A | 11/1994 | Cline et al. |
| 5,373,571 A | 12/1994 | Reid et al. |
| 5,429,635 A | 7/1995 | Purcell, Jr. et al. |
| 5,431,647 A | 7/1995 | Purcell, Jr. et al. |
| 5,441,497 A | 8/1995 | Narciso, Jr. |
| 5,454,807 A | 10/1995 | Lennox et al. |
| 5,483,961 A | 1/1996 | Kelly et al. |
| 5,496,308 A | 3/1996 | Brown et al. |
| 5,496,309 A | 3/1996 | Saadat et al. |
| 5,501,655 A | 3/1996 | Rolt et al. |
| 5,520,681 A | 5/1996 | Fuller et al. |
| 5,530,780 A | 6/1996 | Ohsawa |
| 5,536,265 A | 7/1996 | van den Bergh et al. |
| 5,545,161 A | 8/1996 | Imran |
| 5,607,421 A | 3/1997 | Jeevanandam et al. |
| 5,647,361 A | 7/1997 | Damadian |
| 5,651,785 A | 7/1997 | Abela et al. |
| 5,665,095 A | 9/1997 | Jacobson |
| 5,688,263 A | 11/1997 | Hauptmann et al. |
| 5,702,386 A | 12/1997 | Stern et al. |
| 5,754,717 A | 5/1998 | Esch |
| 5,762,609 A | 6/1998 | Benaron et al. |
| 5,792,100 A | 8/1998 | Shantha |
| 5,800,557 A | 9/1998 | Elhami |
| 5,807,390 A | 9/1998 | Fuller et al. |
| 5,823,941 A | 10/1998 | Shaunnessey |
| 5,824,005 A | 10/1998 | Motamedi et al. |
| 5,830,196 A | 11/1998 | Hicks |
| 5,843,073 A | 12/1998 | Sinofsky |
| 5,855,577 A | 1/1999 | Murphy-Chutorian et al. |
| 5,861,020 A | 1/1999 | Schwarzmaier |
| 5,871,521 A | 2/1999 | Kaneda et al. |
| 5,906,606 A | 5/1999 | Chee et al. |
| 5,908,415 A | 6/1999 | Sinofsky |
| 5,916,153 A | 6/1999 | Rhea, Jr. |
| 5,946,441 A | 8/1999 | Esch |
| 5,947,959 A | 9/1999 | Sinofsky |
| 5,978,541 A | 11/1999 | Doiron et al. |
| 5,997,571 A | 12/1999 | Farr et al. |
| 6,004,315 A | 12/1999 | Dumont |
| 6,039,728 A | 3/2000 | Berlien et al. |
| 6,048,359 A | 4/2000 | Biel |
| 6,071,302 A | 6/2000 | Sinofsky et al. |
| 6,102,905 A | 8/2000 | Baxter et al. |
| 6,106,514 A | 8/2000 | O'Donnell, Jr. |
| 6,113,593 A | 9/2000 | Tu et al. |
| 6,128,522 A | 10/2000 | Acker et al. |
| 6,174,308 B1 | 1/2001 | Goble et al. |
| 6,212,426 B1 | 4/2001 | Swanson |
| 6,241,725 B1 | 6/2001 | Cosman |
| 6,270,492 B1 | 8/2001 | Sinofsky |
| 6,283,958 B1 | 9/2001 | Vogl et al. |
| 6,311,084 B1 | 10/2001 | Cormack et al. |
| 6,315,776 B1 | 11/2001 | Edwards et al. |
| 6,334,315 B1 | 1/2002 | Kotliar |
| 6,343,174 B1 | 1/2002 | Neuberger |
| 6,361,530 B1 | 3/2002 | Mersch |
| 6,381,483 B1 | 4/2002 | Hareyama et al. |
| 6,383,179 B1 | 5/2002 | Neuberger |
| 6,418,252 B1 | 7/2002 | Maitland |
| 6,418,337 B1 | 7/2002 | Torchia et al. |
| 6,503,246 B1 | 1/2003 | Har-Shai et al. |
| 6,506,189 B1 | 1/2003 | Rittman, III et al. |
| 6,542,767 B1 | 4/2003 | McNichols et al. |
| 6,554,824 B2 | 4/2003 | Davenport et al. |
| 6,575,969 B1 | 6/2003 | Rittman, III et al. |
| 6,576,163 B2 | 6/2003 | Mersch |
| 6,579,286 B1 | 6/2003 | Maki et al. |
| 6,802,838 B2 | 10/2004 | Loeb et al. |
| 6,869,430 B2 | 3/2005 | Balbierz et al. |
| 6,996,478 B2 | 2/2006 | Sunshine et al. |
| 7,077,842 B1 | 7/2006 | Cosman |
| 7,171,253 B2 | 1/2007 | Dowlatshahi |
| 7,238,184 B2 | 7/2007 | Megerman et al. |
| 7,270,656 B2 | 9/2007 | Gowda et al. |

(56) References Cited

U.S. PATENT DOCUMENTS

| | | |
|---|---|---|
| 7,274,847 B2 | 9/2007 | Gowda et al. |
| 7,278,993 B2 | 10/2007 | Kelly et al. |
| 7,282,049 B2 | 10/2007 | Orszulak et al. |
| 7,344,529 B2 | 3/2008 | Torchia et al. |
| 7,412,141 B2 | 8/2008 | Gowda et al. |
| 7,609,927 B2 | 10/2009 | Gowda et al. |
| 7,699,838 B2 | 4/2010 | Breen et al. |
| 7,780,679 B2 | 8/2010 | Bobo, Sr. et al. |
| 7,871,406 B2 | 1/2011 | Nields et al. |
| 7,909,817 B2 | 3/2011 | Griffin et al. |
| 7,942,870 B2 | 5/2011 | Berzak et al. |
| 8,211,095 B2 | 7/2012 | Gowda et al. |
| 8,394,099 B2 | 3/2013 | Patwardhan |
| 8,644,907 B2 | 2/2014 | Hartmann et al. |
| 8,851,080 B2 | 10/2014 | Gowda et al. |
| 9,339,336 B2 | 5/2016 | Gowda et al. |
| 9,403,029 B2 | 8/2016 | Gowda et al. |
| 10,433,909 B2 | 10/2019 | Gowda et al. |
| 10,869,721 B2 | 12/2020 | Gowda et al. |
| 10,881,443 B2 | 1/2021 | Curley |
| 2002/0111615 A1 | 8/2002 | Cosman et al. |
| 2002/0120261 A1 | 8/2002 | Morris et al. |
| 2002/0193800 A1 | 12/2002 | Kienzle et al. |
| 2003/0212394 A1 | 11/2003 | Pearson et al. |
| 2003/0233052 A1 | 12/2003 | Kokate et al. |
| 2004/0039429 A1 | 2/2004 | Daniel et al. |
| 2004/0078036 A1 | 4/2004 | Keidar |
| 2004/0181216 A1 | 9/2004 | Kelly et al. |
| 2005/0065515 A1 | 3/2005 | Jahng |
| 2005/0075649 A1 | 4/2005 | Bova et al. |
| 2005/0131399 A1 | 6/2005 | Loeb et al. |
| 2005/0177210 A1 | 8/2005 | Leung et al. |
| 2006/0079887 A1 | 4/2006 | Buysse et al. |
| 2006/0084867 A1 | 4/2006 | Tremblay et al. |
| 2006/0149280 A1 | 7/2006 | Harvie et al. |
| 2006/0184163 A1 | 8/2006 | Breen et al. |
| 2007/0232898 A1 | 10/2007 | Huynh et al. |
| 2007/0239150 A1 | 10/2007 | Zvuloni et al. |
| 2007/0239169 A1 | 10/2007 | Plaskos et al. |
| 2007/0249938 A1 | 10/2007 | Shields |
| 2008/0004481 A1 | 1/2008 | Bax et al. |
| 2008/0185314 A1 | 8/2008 | Tomasello et al. |
| 2008/0200798 A1 | 8/2008 | Eklund et al. |
| 2009/0198309 A1 | 8/2009 | Gowda et al. |
| 2009/0292279 A1 | 11/2009 | Bliweis et al. |
| 2010/0185087 A1 | 7/2010 | Nields et al. |
| 2011/0040172 A1 | 2/2011 | Carpentier et al. |
| 2011/0258842 A1 | 10/2011 | Dukesherer et al. |
| 2012/0245573 A1 | 9/2012 | Gowda et al. |
| 2013/0053867 A1 | 2/2013 | Gowda et al. |
| 2013/0123598 A1 | 5/2013 | Jenkins et al. |
| 2013/0165937 A1 | 6/2013 | Patwardhan |
| 2014/0012155 A1 | 1/2014 | Flaherty et al. |
| 2014/0088575 A1 | 3/2014 | Loeb |
| 2015/0030050 A1 | 1/2015 | Skliar et al. |
| 2015/0094698 A1 | 4/2015 | Gowda et al. |
| 2015/0257830 A1 | 9/2015 | Tyc et al. |
| 2016/0151639 A1 | 6/2016 | Scharf et al. |

FOREIGN PATENT DOCUMENTS

| | | |
|---|---|---|
| CN | 103442631 A | 12/2013 |
| DE | 4137983 A1 | 6/1992 |
| EP | 0361762 A2 | 4/1990 |
| EP | 0995406 A1 | 4/2000 |
| EP | 1689464 A2 | 8/2006 |
| EP | 2285307 A1 | 2/2011 |
| EP | 2412403 A2 | 2/2012 |
| JP | 2000217835 A | 8/2000 |
| JP | 2001046523 A | 2/2001 |
| JP | 200310233 A | 1/2003 |
| JP | 2004530469 A | 10/2004 |
| JP | 2009/524469 A | 7/2009 |
| JP | 2011516184 A | 5/2011 |
| JP | 201596193 A | 5/2015 |
| JP | 2016502434 A | 1/2016 |
| WO | 8903665 A1 | 5/1989 |
| WO | 9614880 A1 | 5/1996 |
| WO | 9720515 A1 | 6/1997 |
| WO | 9932184 A1 | 7/1999 |
| WO | 99032184 A1 | 7/1999 |
| WO | 9942044 A1 | 8/1999 |
| WO | 99042044 A1 | 8/1999 |
| WO | 01095822 A2 | 12/2001 |
| WO | 2002000298 A1 | 1/2002 |
| WO | 0218011 A1 | 3/2002 |
| WO | 03065880 A2 | 8/2003 |
| WO | 2005046753 A2 | 5/2005 |
| WO | 2006055554 A2 | 5/2006 |
| WO | 2006078677 A2 | 7/2006 |
| WO | 07005830 A2 | 1/2007 |
| WO | 07090288 A1 | 8/2007 |
| WO | 2007086056 A2 | 8/2007 |
| WO | 2007090288 A1 | 8/2007 |
| WO | 2009060394 A1 | 5/2009 |
| WO | 2009-125002 A1 | 10/2009 |
| WO | 2009124301 A1 | 10/2009 |
| WO | 2012071388 A2 | 5/2012 |

OTHER PUBLICATIONS

Japanese Office Action regarding Patent Application No. 2018555980, dated Apr. 18, 2022.
European Office Action regarding Application No. 17722616.4, dated Nov. 25, 2021.
Communication pursuant to Article 94(3) EPC dated Sep. 12, 2014 for European Application No. 09 726 951.8-1652.
Communication under Rule 71(3)EPC dated Jul. 7, 2016 for European Application No. 09725941.8-1666.
European Search Report dated Jun. 30, 2017 for European Application No. 16197308.6.
European Search Report mailed Mar. 17, 2017 for EP Application No. 16197308.6.
International Preliminary Report and Written Opinion mailed on May 10, 2010 for PCT/US2009/39568 claiming benefit of U.S. Appl. No. 61/042,199, filed Apr. 3, 2008.
International Preliminary Report on Patentability mailed Nov. 8, 2018 in corresponding/related International Application No. PCT/US2017/029896.
International Preliminary Report on Patentability with Written Opinion mailed on May 30, 2007 for PCT/US04/37244 claiming benefit of U.S. Appl. No. 10/703,304, filed Nov. 7, 2003.
International Search Report and Written Opinion mailed Jul. 7, 2017 in corresponding International Application No. PCT/US2017/029896.
International Search Report and Written Opinion mailed on Jul. 16, 2009 for PCT/US2009/39568 claiming benefit of U.S. Appl. No. 61/042,199, filed Apr. 3, 2008.
International Search Report with Written Opinion mailed on Apr. 10, 2007 for PCT/US04/37244 claiming benefit of U. S. U.S. Appl. No. 10/703,304, filed Nov. 7, 2003.
Japanese Office Action mailed Jun. 9, 2015 for JP Patent Application No. 2011-503237 (7 pages) with English translation.
Kim "Materials for multifunctional balloon catheters with capabilities in cardiac electrophysiological mapping and ablation therapy" NMAT2971, 8 pages, 2011.
Ninth New Collegiate Dictionary, Copyright 1988 by Merriam-Webster Inc., Springfield, MA, p. 768.
Office Action mailed Apr. 29, 2020 in corresponding/related Chinese Application No. 201780038816.5.
Office Action mailed Oct. 26, 2021, in corresponding Japanese Application No. 2018-555980.
Office Action regarding Japanese Patent Application No. 2018-555980, dated Feb. 24, 2021.
Partial European Search Report dated Mar. 17, 2017 for European Application No. 16197308.6.
Second Office Action regarding Chinese Patent Application No. 201780038816.5 dated Jan. 15, 2021.

(56) References Cited

OTHER PUBLICATIONS

U.S. Appl. No. 10/208,222, filed Jul. 30, 2002 entitled "Cooled Tip Laser Catheter for Sensing and Ablation of Cardiac Arrhythmias."
U.S. Appl. No. 10/703,304, filed Nov. 7, 2003 entitled "Cooled Laser Fiber for Improved Thermal Therapy".
Weber et al., "Laser versus Radiofrequency Catheter Ablation of Ventricular Myocardium in Dogs: A Comparative Test," Cardiology, vol. 88, 1997, pp. 346-352.
Welch et al., "Evaluation of Cooling Techniques for the Protection of the Epidermis During Nd: YAG Laser Irradiation of the Skin," in Neodymium-YAG Laser in Medicine and Surgery, S.N. Joffe, Ed. New York: Elsevier, 1983, pp. 196-204.
Zhou "Piezoelectric films for high frequency ultrasonic transducers in biomedical applications" Prog Mater Sci., 56(2):139-174, Feb. 2011.

NAVIGATION AND LOCAL THERMOMETRY

CROSS-REFERENCE TO RELATED APPLICATIONS

This application is a continuation of U.S. patent application Ser. No. 15/141,282 filed on Apr. 28, 2016. The entire disclosure of the above application is incorporated herein by reference.

FIELD

The subject application relates generally to a temperature measuring system, and particularly to a system for measuring a temperature within a volume.

BACKGROUND

A procedure can be performed on a subject that may include heating a selected portion of a subject. For example, a heating device can be positioned within a portion of the subject to heat the portion of the subject. After heating a portion of the subject, changes may occur at or near the device generating the heat or thermal energy. During a surgical procedure, selected tissues may die due to the generated heat. After a selected period of time the device generating the thermal energy may be removed to complete at least a portion of the procedure.

SUMMARY

When performing a procedure on a subject, tissues may be interacted with to create a selected result. For example, tissues may be heated to a selected degree to kill the tissue. For example, tumors may be heated to be killed. The tissues may then be removed with various processes, such as natural waste removal processes. The tumor may also be heated to a degree to completely remove the tissue.

It is understood, however, that non-human tissue or non-living structures may also be acted upon. For example, an instrument can be positioned within a non-living structure to heat or interact with a select portion of the structure to obtain a select result. For example, an instrument or a probe may be positioned within a volume of water or a gelatin material to interact with a selected portion of the structure.

To interact with a structure or volume, it may be selected to heat a portion of the volume to a selected temperature. Measuring the temperature within the volume, however, may include measuring a temperature of the structure a selected distance away from the surface of the instrument. For example, an instrument can be inserted into the volume. The instrument can heat tissue or a portion of the volume substantially adjacent to the instrument and the thermal energy may transfer away from the instrument. Such transfer of thermal energy may be dependent on the type of tissue, circulation around the instrument, and other factors. Accordingly, a precise determination of the temperature at a distance away from the instrument may be difficult to determine and/or predict. Accordingly, a temperature sensing instrument can be incorporated into the instrument to measure a temperature a distance away from the instrument heating the volume.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
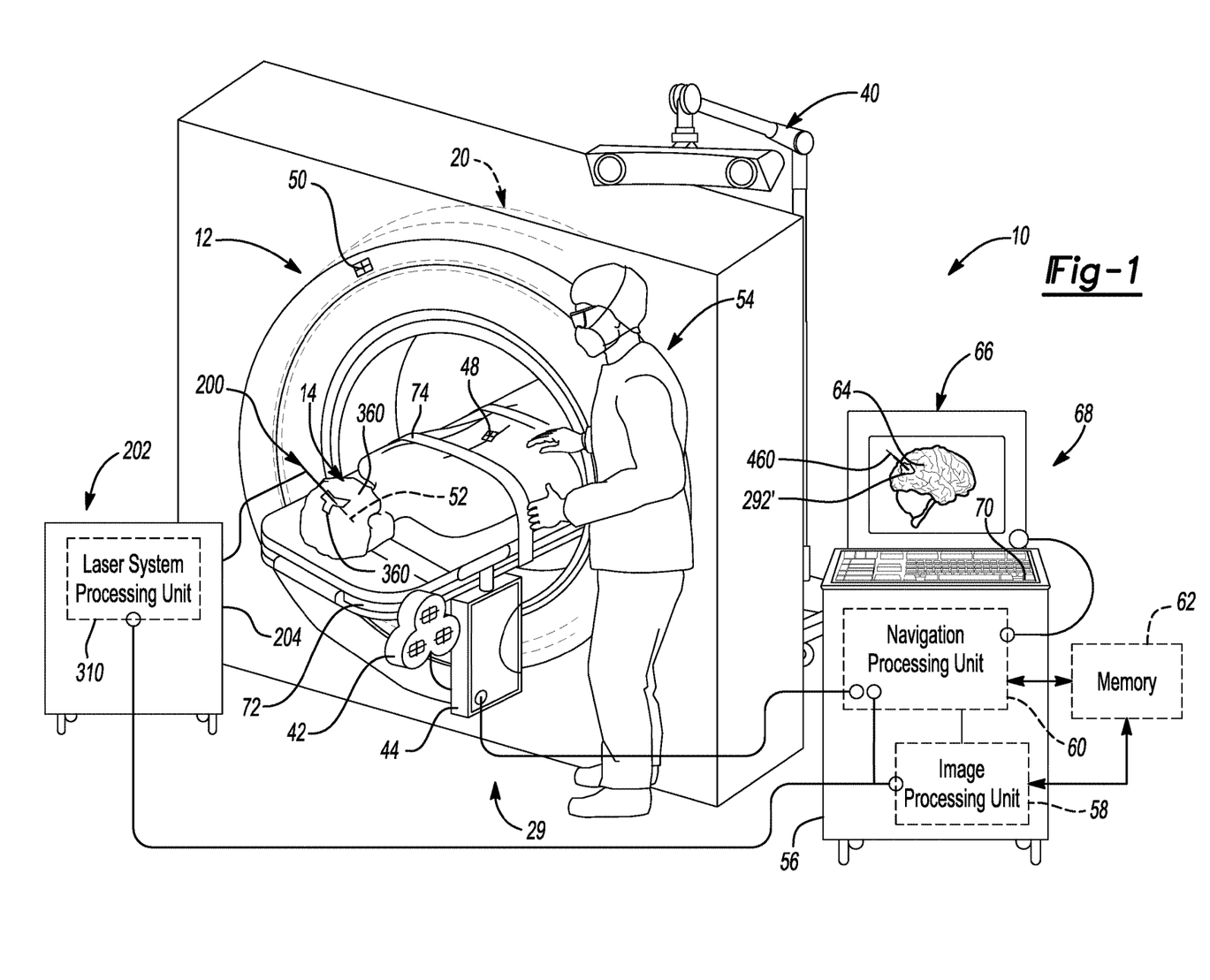
FIG. 1 is an environmental view of an operating theatre including an optional imaging system and a navigation system.

Illustrated in FIG. 1 is a diagrammatic overview of a system including various components, such as a navigation system 10 and an imaging system 12. The various components may be included in a surgical suite or may be in separate locations for various portions of a procedure on a patient 14 or any appropriate selected subject. Non-human and non-living subjects may also be subjected to a procedure using the various components illustrated in FIG. 1.

The navigation system 10 can be used to navigate a device (e.g. a medical device 200 as discussed further herein) into or relative to the subject 14. A tracking system 29 may be used to track the device 200 to assist in determining a position (including location and orientation). The device may include an implant or an instrument that is moved relative to the subject 14. It should further be noted that the navigation system 10 may be used to navigate any type of instrument, implant, or delivery system, including: guide wires, arthroscopic systems, orthopedic implants, spinal implants, deep brain stimulation (DBS) leads, cardiac pacing leads, ablation instruments, etc. Moreover, the instruments may be used to navigate or map any region of the body. The navigation system 10 and the various tracked items may be used in any appropriate procedure, such as one that is generally minimally invasive or an open procedure.

The navigation system 10 can interface with the imaging system 12 that is used to acquire image data of the subject or patient 14. The image data may be pre-operative, intra-operative, or post-operative, or real-time image data of the patient 14. The real time image data may be substantially instantaneous image data that may allow a user 54 and/or various processing units, as discussed herein, to analyze a portion of the subject 14 to act upon during a procedure. It will be understood by one skilled in the art, any appropriate subject can be imaged and any appropriate procedure may be performed relative to the subject. The subject may be a human patient and the procedure may be a surgical procedure, such as an implantation of a device (e.g. a screw, lead, etc.).

Exemplarily illustrated in FIG. 1, the imaging system 12 includes a magnetic resonance imaging (MRI) system. The MRI system may be operated in a manner that is generally understood by one skilled in the art. Exemplary MRI systems include the SIGNA™ MRI sold by the General Electric Company; the SIGNA™ MRI is available in various configurations. The imaging system may, however, also include an O-arm® imaging device sold by Medtronic Navigation, Inc. having a place of business in Louisville, Colorado, USA, the imaging system may include those discloses in U.S. Pat. Nos. 7,188,998; 7,108,421; 7,106,825; 7,001,045; and 6,940,941; all of which are incorporated herein by reference or other appropriate imaging system, including x-ray C-arm systems, PET imaging systems, etc.

The imaging device 12 may have a gantry housing 20 that encloses an image capturing portion 22. The image capturing portion 22 may include portions generally used in a MRI, including magnets, radio frequency (RF) emitters and receivers, etc. An x-ray imaging system may include an x-ray source or emission portion and an x-ray receiving or image receiving portion located generally or as practically possible 180 degrees from each.

The position of the image capturing portion 22 can be precisely known relative to any other portion of the imaging device 12. In addition, as discussed herein, the precise knowledge of the position of the image capturing portion 22 can be known or determined with the imaging processing system or with the tracking system 29. The position of the image capturing portion 22, while gathering image data, may be used during navigation of the device 200. The position of the patient 14 may also be determined by tracking a patient tracking device 48 that may be placed on the patient 14 to track the patient 14 during image data acquisition.

The tracking system 29 can include various portions that are associated or included with the navigation system 10. The tracking system 29 can also include a plurality of types of tracking systems including an optical tracking system that includes an optical localizer 40 and/or an electromagnetic (EM) tracking system that can include an EM localizer 42. The optical localizer 40 may "view" or optically track trackable portions (tracking devices) with cameras. The EM localizer 42 may generate a field and a trackable portion (e.g. EM tracking device) may sense the field to determine a location relative to another tracking device in the field. One skilled in the art will also understand that the EM tracking device may emit a signal that is sensed or received by the localizer 42 for determining a position of the tracking device. Various tracking devices, including those discussed further herein, can be tracked with the tracking system 29 and the information can be used by the navigation system 10 to allow for a display of a position of an item. Briefly, tracking devices, such as the patient tracking device 48, an imaging device tracking device 50, and an instrument tracking device 52, 370, allow selected portions of an operating theater to be tracked relative to one another with the appropriate tracking system 29, including the optical localizer 40 and/or the EM localizer 42.

It will be understood that any of the tracking devices 48-52 can be optical or EM tracking devices, or both, depending upon the tracking localizer used to track the respective tracking devices. It will be further understood that any appropriate tracking system can be used with the navigation system 10. Alterative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colorado Exemplary tracking systems are also disclosed in U.S. Pat. No. 8,644,907, issued Feb. 4, 23012, titled "Method And Apparatus For Surgical Navigation"; U.S. Pat. No. 7,751,865, titled "Method And Apparatus For Surgical Navigation", issued Jul. 6, 2010; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all incorporated by reference herein.

Further, for EM tracking systems it may be necessary to provide shielding or distortion compensation systems to shield or compensate for distortions in the EM field generated by the EM localizer 42. Exemplary shielding systems include those in U.S. Pat. No. 7,797,032, titled "Method and system for navigating a catheter probe in the presence of field-influencing objects", issued on Sep. 14, 2010 and U.S. Pat. No. 6,747,539, titled "Patient-shielding and coil system", issued on Jun. 8, 2004, all of which are incorporated herein by reference. Distortion compensation systems can include those disclosed in U.S. Pat. No. 6,636,757, titled "Method and apparatus for electromagnetic navigation of a surgical probe near a metal object", issued on Oct. 21, 2003, all of which are incorporated herein by reference.

With an EM tracking system, the EM localizer 42 and the various tracking devices can communicate through an EM controller 44. The EM controller may include various amplifiers, filters, electrical isolation, and other systems. The EM controller 44 can also control one or more conductive coils of the localizer 42 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 44.

It will be understood that the tracking system may also be or include any appropriate tracking system, including a STEALTHSTATION® TRIA®, TREON®, and/or S7™ Navigation System having an optical localizer, similar to the optical localizer 40, sold by Medtronic Navigation, Inc. having a place of business in Louisville, Colorado Optical tracking systems may also include those disclosed in U.S. Pat. No. 8,010,177, Aug. 30, 2011, Intraoperative Image Registration" and/or U.S. Pat. No. 6,235,038, issued on May 22, 2001, titled "System For Translation Of Electromagnetic And Optical Localization Systems", all incorporated herein by reference.

Although discussed herein is the EM tracking system using the EM localizer 42, it is understood that other appropriate tracking systems may be used in place of the EM tracking system or to augment the EM tracking system. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 12 can further include a separate image processing unit 58 that can be housed in a selected location, such as on a server system, in a remote access location, or at a local location such as in a cart 56. The navigation system 10 can include the navigation processing unit 60 that can communicate or include a memory 62. The memory 62 may also communicate with the image processing unit 58. The memory 62 may be a selected non-transient computer readable memory. Exemplary memory systems may include dynamic random access memory (DRAM), magnetic alterable media, physical read/write media, and the like. The memory 62 may store various information or instructions, including computer executable instructions. The navigation processing unit 60 can receive information, including image data, from the imaging system 12 and tracking information from the tracking systems 29, including the respective tracking devices 48-52 and the localizers 40-42. Image data can be displayed as an image 64 on a display device 66 of a workstation or other computer system 68. The workstation 68 can include appropriate input devices, such as a keyboard 70. It will be understood that other appropriate input devices can be included, such as a mouse, a foot pedal or the like. The various processing units and computers or workstations may include internal or local memory and processing units. The processing units may include central processing units that are general computers that execute instructions to perform tasks on a chip. The processing units may also be or include circuits, such as specific circuits including application specific integrated circuits (ASIC). Accordingly, the processing units may be devices that receive information and execute instructions that are stored or received based on the information.

The image processing unit 58 receives and/or processes image data from the imaging system 12 and transmits it to the navigation processing unit 60. It will be further understood, however, that the imaging system 12 need not perform any image processing and it can transmit the image data directly to the navigation processing unit 60. Accordingly, the navigation system 10 may include or operate with a single or multiple processing centers or units that can access single or multiple memory systems based upon system design. The imaging processing unit 58 may also be used to control the imaging system 12. Further, the imaging processing unit may be used to determine selected positions or areas of interest of the patient to image based on selected inputs and/or instructions. For example, a tracked position of the instrument 200 may be determined and transmitted to the image processing unit 58 and the region of the patient 14 around the tracked position of the instrument 200 may be selected to be imaged.

The patient 14 can be fixed onto a table 72, but is not required to be fixed to the table 72. The table 72 can include a plurality of straps 74. The straps 74 can be secured around the patient 14 to fix the patient 14 relative to the table 72. Various apparatuses may be used to position the patient 14 in a static position on the operating table 72. Examples of such patient positioning devices are set forth in commonly assigned U.S. patent application Ser. No. 10/405,068, published as U.S. Pat. App. Pub. No. 2004/0199072, entitled "An Integrated Electromagnetic Navigation And Patient Positioning Device", filed Apr. 1, 2003, which is hereby incorporated by reference. Other known apparatuses may include a Mayfield® clamp.

Also, the position (including three-dimensional location and orientation) of the patient 14 relative to the imaging system 12 can be determined by the navigation system 10 with the patient tracking device 48 and the imaging system tracking device 50. The imaging system 12, such as the MRI can know a position at which image data is acquired and can be repositioned or operated to acquire image data at the same position at a later time. Knowing the relative position of the patient 14 may then allow the patient 14 to also be repositioned to collect a second image data later than a first image data of substantially the same region of the patient 14.

Subject or patient space (a volume in and around the patient in real space) and image space (a volume defined by the image data) can be registered by identifying matching points or fiducial points in the patient space and related or identical points in the image space. The imaging device 12 can be used to generate image data at a precise and known position. This can allow image data that is automatically or "inherently registered" to the patient 14 upon acquisition of the image data. Essentially, the position of the patient 14 is known precisely relative to the imaging system 12 due to the accurate positioning of the imaging system 12 relative to the patient 14. Also, the exact position of the area from which image data is acquired is known or can be determined. This allows points in the image data to be known relative to points of the patient 14 because of the known precise location of the imaging system 12.

Alternatively, manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, now published U.S. Pat. App. Pub. No. 2010/0228117, incorporated herein by reference.

Once registered, the navigation system 10 with or including the imaging system 12, can be used to perform selected procedures. Selected procedures can use the image data generated or acquired with the imaging system 12. Further, the imaging system 12 can be used to acquire image data at different times relative to a procedure. As discussed herein, image data can be acquired of the patient 14 subsequent to a selected portion of a procedure for various purposes, including confirmation of the portion of the procedure.

With continuing reference to FIG. 1, the imaging system 12 can generate actual or virtual three dimensional images of the patient 14. The patient 14 can be placed relative to the imaging system 12 to allow the imaging system 12 to obtain image data of the patient 14. To generate 3D image data, the image data can be acquired from a plurality of views or positions relative to the patient 14. The 3D image data of the patient 14 can be used alone or with other information to assist in performing a procedure on the patient 14 or an appropriate subject. It will be understood, however, that any appropriate imaging system can be used, including magnetic resonance imaging, computed tomography, fluoroscopy, etc. to acquire image data (including 3D image data) of the patient 14.

As noted above, with reference to FIG. 1, the surgical navigation system 10 can be used to navigate the instrument 200 for a selected procedure. With additional reference to FIG. 2, according to various embodiments, the device may be a laser energy system 202 that may be used to perform a selected procedure on a subject, such as the human patient. The laser system 202 can include the laser system as disclosed in U.S. Pat. Nos. 7,270,656; 8,211,095; 8,851,080; and U.S. Patent Application Publication No. 2012/0245573 published on Sep. 27, 2012, all of the above incorporated herein by reference.

Figure 2:
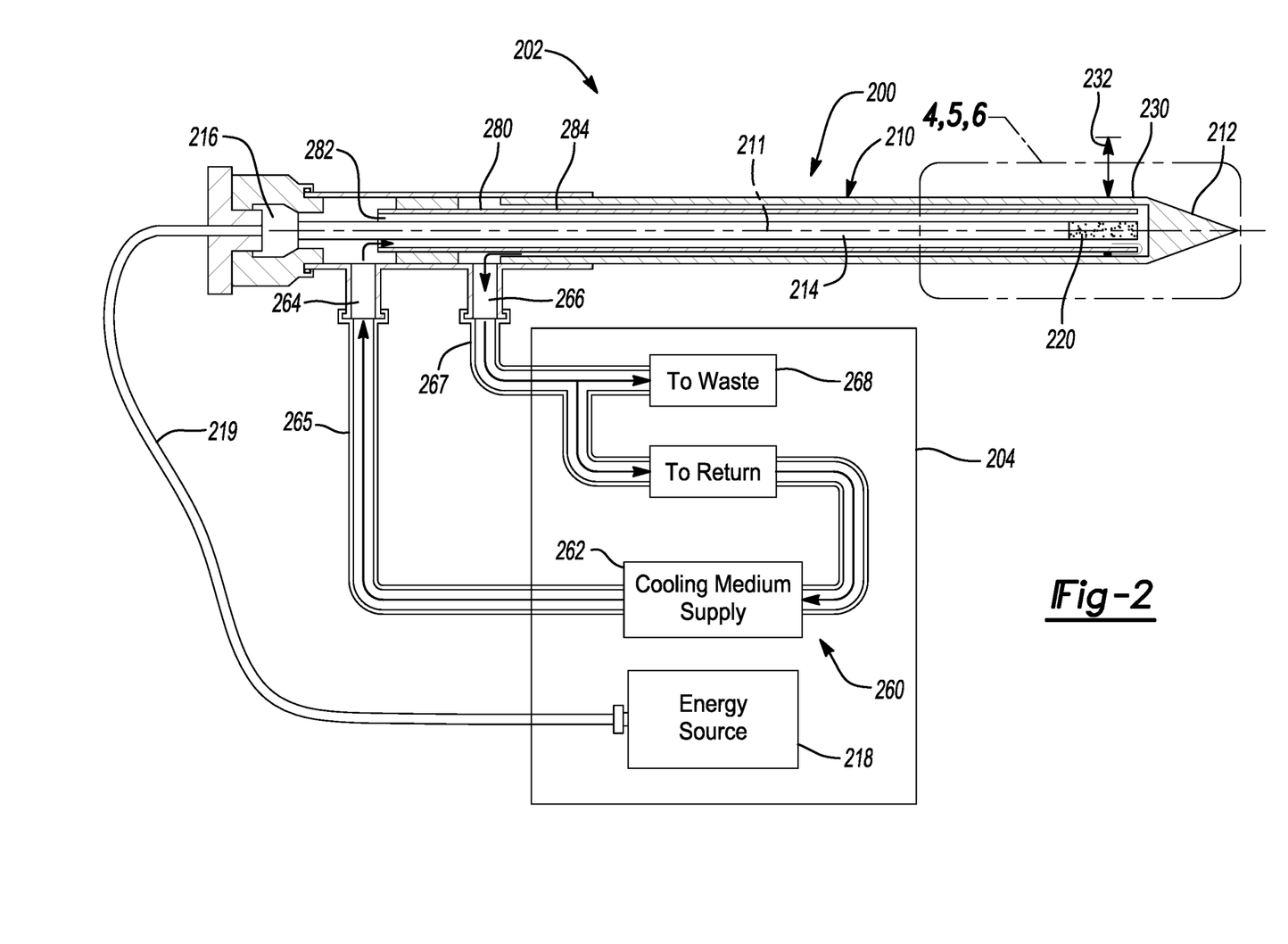
FIG. 2 is a schematic view of a laser heating system.

Generally, the laser system 202 includes the instrument 200. The instrument 200 may include a housing 210 which may be rigid, flexible, or semi-rigid. For example, the housing 210 can be formed to include a selected rigidity for insertion into a patient, such as into brain tissue of the subject through a selected bore formed in a skull of the subject. The housing may include or define an internal bore. The internal bore may be blind bore that is terminated at a distal end by a distal tip 212. The distal tip 212 may be substantially solid and may include an exterior cutting surface, if selected. The laser system 202 generally includes an energy delivering component 214 that may be housed in in the housing and extends from a proximal portion 216 that can be coupled to an energy source 218. The energy source may be in a housing 204 and connected with a line 219 (e.g. a fiber optic line which may have a cladding 219a) with the energy delivery component 214.

The energy delivery component 214 can extend from the proximal end 216 to a distal end 220. At the distal end 220 the energy delivery component 214 can deliver energy from the energy source 218 to create a selected result. For example, the energy source 218 can deliver a selected light energy (such as a laser light energy) to the proximal end 216 of the energy delivery component 214. The energy delivery component 214 may act as a wave guide so that the light energy travels to the distal end 220 to be emitted. For example, the housing 210 may be transparent such that the light energy is emitted through the housing 210 to effect adjacent tissue and the tissue that is a distance from the housing 210. For example, as discussed herein, the housing 210 can include an exterior surface 230. Therefore, some matter, such as brain tissue, may contact the exterior surface 230 and receive the light energy. Further, tissue that is a distance away from the surface 230, such as a distance 232 may also receive a selected amount of the energy from the energy delivery component 214.

Figure 3:
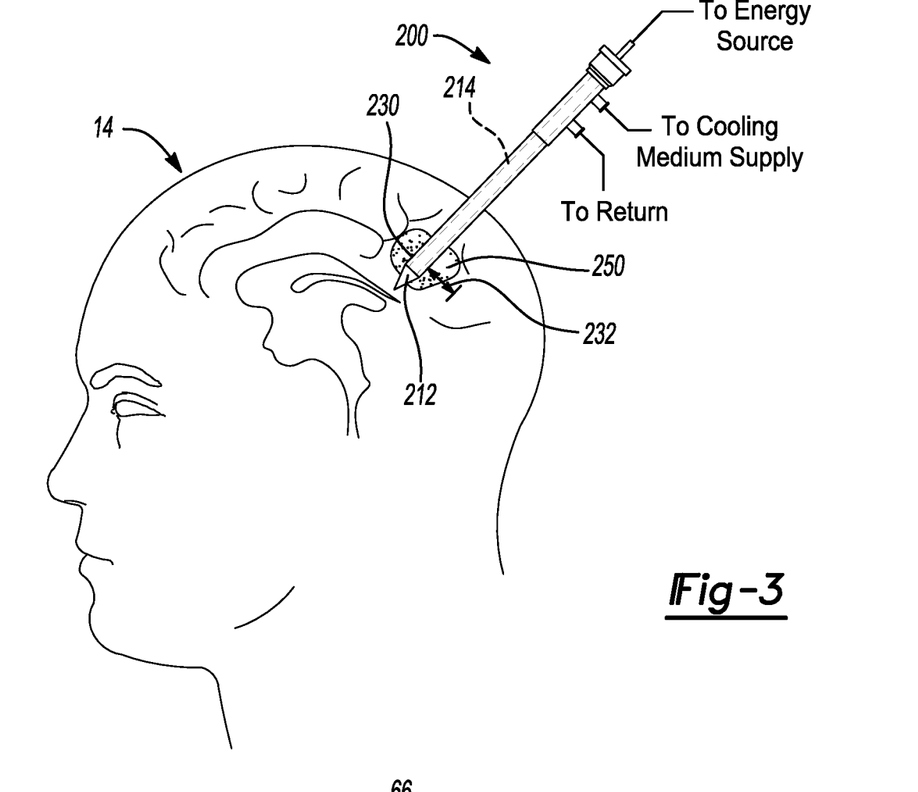
FIG. 3 is a schematic illustration of a use of the laser heating system, according to various embodiments.

As the energy is received and absorbed in the tissue, including the tissue that may contact the surface 230 of the housing 210 and tissue that is the distance 232 away from the housing 210, a temperature increase may occur in the tissue. As illustrated in FIG. 3, the device 200 may be positioned within a portion of the patient 14. The distal solid end of the housing 212 may penetrate to a selected region and the energy delivery component 214 can be positioned within the housing 210. As also illustrated in FIG. 3, tissue may contact the external surface 230 of the housing 210 and the tissue may also be positioned the distance 232 away from the housing 210. The thermal energy may be directed at a selected region or region or area of interest 250. The region of interest may include a tumor (schematically illustrated in FIG. 3). The tissue may be heated to a selected degree when energy is delivered through component 214, including tissue that contacts the housing 210 at the surface 230 and the tissue at the distance 232 away from the housing 210.

According to a selected procedure, heating the tissue to a selected degree may include heating the tissue to a specific temperature or within a specific temperature range. To assist in achieving a selected temperature, a cooling system 260 may also be included within the housing 204. The cooling system 260 may assist in regulating a temperature of the device 200.

The cooling system 260 may include a cooling medium supply 262 that delivers a cooling medium to an inlet port 264 through a supply line 265 into the housing 210. An exit port 266 can allow used or waste coolant to exit the housing 210 through line 267. In various embodiments, the cooling material can be recycled into the cooling medium supply 262 or may be delivered to a waste container 268.

The cooling medium from the cooling supply 262 may travel through passages formed within the housing 210 at least by a first assembly or sheath 280. The sheath 280 may extend along at least a selected portion of the length of the energy delivery component 214 and form a first channel 282 that allows for direct contact between the energy delivery component 214 and the cooling fluid and a second channel 284 that is formed between an inner wall of the housing 210 and the sheath 280. Again, flow of a coolant for cooling the medical instrument 200 is disclosed in U.S. Patent Application Publication 2012/0245573, incorporated herein by reference.

During use the energy delivered by the energy delivery component 214 heats the tissue, such as the tissue of the region of interest 250. The temperature selected to be achieved in the region of interest 250 can be based on various factors, including the size of the tumor, type of tumor, or other selected features. Further, different procedures may require or select a different temperature or temperature range, such as affecting healthy brain tissue for a selected region or for affecting the delivery of a pharmaceutical, such as a heat activated pharmaceutical. Nevertheless, a temperature of the tissue within the region of interest 250 may be selected to be determined.

Figure 4:
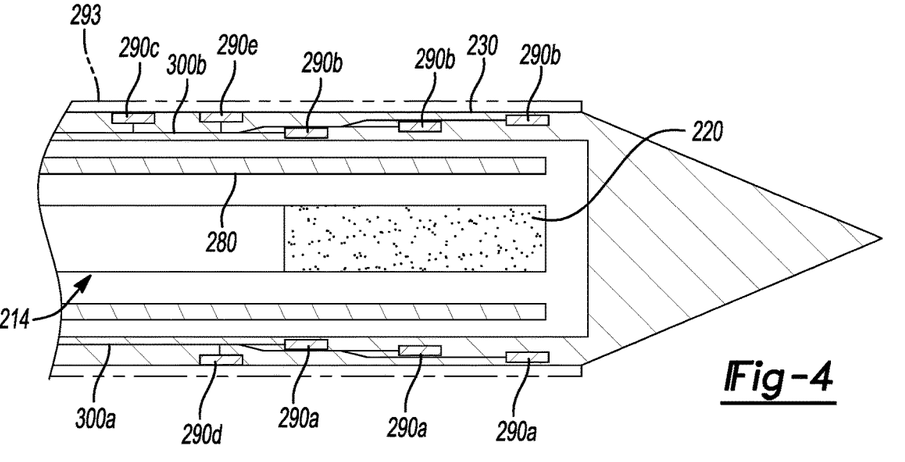
FIG. 4 is a detail view of a distal end of an instrument of the laser heating system.

A temperature sensing component may be used to assist in measuring a temperature of the region of interest 250. One or more temperature components may be included in the laser system 202. In various embodiments, as illustrated in FIG. 4, a first temperature sensing component 290a and a second temperature sensing component 290b can be incorporated into the instrument 200. The temperature sensing components 290a, 290b can be substantially similar or identical to one another, but be positioned at different locations, such as at opposite sides of the instrument 200 or at any appropriate angularly offset position relative to one another. Further, it will be understood, that the temperature sensing components 290a, 290b can be positioned axially along a length of the instrument 200. For example, the temperature sensing components can be substantially equally spaced along a length of the energy delivery component 214, such as a third temperature sensing component 290c may be axially spaced from the first and second temperature sensing component 290a, 290b. Also, the third temperature sensing component may include a plurality of the third temperature sensing component any may also be at various circumferential positions around the energy delivery component 214.

As discussed above, the temperature sensing component 290a, 290b, and 290c may all be substantially identical temperature-sensing components such as those discussed herein. For example, the temperature sensing components 290a, 290b, and 290c may all be distant temperature-sensing components that sense a temperature distant or a relative temperature at a distance from the exterior surface 230 at the housing 210. It is further understood that additional temperature-sensing components, including a fourth temperature-sensing component 290d and a fifth temperature-sensing component 290e may be included with the laser system 202 such as being incorporated into the instrument 200. The fourth and fifth temperature-sensing components 290d, 290e may be axially and angularly positioned relative to the other temperature-sensing components 290a, 290b, and 290c and any appropriate number may be included in the instrument 200. According to various embodiments, fourth and fifth temperature-sensing component 290d, 290e may be a different type of temperature-sensing component than the first through third temperature-sensing components 290a, 290b, and 290c. For example, the fourth and fifth temperature-sensing components 290d, 290e may be contact temperature-sensing components, including those discussed further herein. The contact temperature-sensing components can be used to measure or determine a temperature substantially adjacent to the surface 230 of the housing 210. Therefore, temperature-sensing components can include those that measure a temperature both at the surface 230 and a distance away from the surface 230 of the instrument 200. This may allow the laser system 202 to be used to determine temperatures at different locations relative to the housing 210, as discussed above and allowed to be illustrated as the icon 292'.

Further, the temperature-sensing component 290a-290e can be incorporated into the housing or relative to the energy conducting component 214 in various manners. For example, the temperature-sensing components 290a-290e may be embedded into the housing 210 near the surface 230. Various processes may be used such as co-extrusion or molding of the temperature-sensing components 290a-290e into the housing 210. According to various embodiments, the temperature-sensing components may also be encased between a surface of the housing 210 and an optional exterior coating or layer 293 that may be positioned over the temperature-sensing components 290a-290e. The exterior surface of the overcoating 293 (illustrated in phantom) would then be the exterior surface 230 of the housing 210. The exterior surface of the overcoating 293 would be the surface that is in direct contact with a volume, including the tissue of the subject 14. It is understood, however, that various manufacturing techniques may be employed to position the temperature-sensing components 290a-290e with the instrument 200.

The temperature sensing component(s), regardless of the number included with the medical device 200, can include an ability to measure or sense a temperature in the region of interest. The temperature sensors components may sense a temperature at the surface 230 and at various selected distances from the surface 230 of the housing 210, including at least the distance 232 away from the surface 230 of the housing 210.

Various temperature sensors can include direct temperature sensors such as thermistors, thermo-couples, or resistance temperature detectors, which can include thin film resistant temperature detectors. One example of a contact or direct temperature sensor includes the sensor disclosed in DH Kim et. al., Materials for multifunctional balloon catheters with capabilities in cardiac electrophysiological mapping and ablation therapy, Nature Materials, 10, 316-323 (March 2011), doi:10.1038/nmat2971. The direct temperature sensors are able to sense a temperature or measure a temperature substantially in contact with the temperature sensor. Therefore, the temperature sensor 290a, 290b can measure a temperature substantially at the surface 230 of the housing 210.

The temperature sensor 290a, 290b however, may also include more than one type of temperature sensor. Accordingly, indirect temperature sensors may also be included with one or more temperature sensors 290a, 290b. For example, two temperature sensors may be positioned relative to another, such as next to one another, to form the temperature sensor components 290a, 290b. Each of the temperature sensor components 290a, 290b may measure both a direct temperature at the surface 230 and a temperature at least at the distance 232 away from the surface 230.

Indirect temperature sensors may be used to measure a temperature at least the distance 232 away from the surface 230 in various manners. For example, indirect temperature sensors can include a low frequency response, including mechanical response or elastic response in an electromechanical transducer. High frequency response, such as a high frequency mechanical ultrasound response can also be used, such as in piezoelectric sensor or ultrasound temperature sensors as discussed below. Electrical capacitors and resistance may also be used to sense a temperature at a distance from the surface 230.

Further indirect temperature sensors can include sensing channels that can sense or receive optical emissions. For example, the temperature sensor components 290a, 290b can include a sensor or optical channel that receives an optical emission from black body radiation or chemical fluorescent such as photoelectric sensors (e.g., polyallylamine hydrochloride thin film or optical fiber receptors). The perceived or sensed optical or infrared emissions can be analyzed for intensity or frequency or both (e.g. spectroscopically). Further optical coherence tomography or optical scattering can also be analyzed at optical sensors based upon a transmission from a fiber optic element and sensing return of interference intensity, and frequency analysis.

In various embodiments, the ultrasound temperature sensors can include sensors such as those disclosed in Q Zhou et. al. Piezoelectric films for high frequency ultrasonic transducers in biomedical applications, Prog. Mater. Sci. 56, 139-174, (2011), doi:10.1016/j.pmatsci.2010.09.001). The temperature sensors can generally sense a range of temperatures of about 30° Celsius (C) to about 90° C. Alternatively, the temperature sensors can be used to determine a differential or boundary of a differential such as about a 1° difference to about a 5° difference. Further various optical or sensing channel temperature sensors can include the temperature sensor Fiber Optic Temperature Probe PRB-MR1 sold by OSENSA Innovations Corp. having a place of business at Coquitlam, BC, Canada.

The temperature sensor components 290a, 290b can transmit the sensed information, such as ultrasound reflections or optical information and transmit the information along transmission lines 300a and 300b, respectively. The transmission lines 300a and 300b can include wired or wireless transmissions to a selected analyzing system, including the navigation processing unit 60 or the imaging processing unit 58. It is understood that the laser system 202 may also include a laser system processing unit 310. The laser system processing unit 310 may be similar to the other processing units, and all of the processing units may be incorporated as computer executable instructions on one processing unit. Nevertheless, the laser processing unit may receive signals from the temperature sensor components 290a, 290b via the lines 300a, 300b. The laser processing unit 310 may also alter operation or provision of power to the energy conducting component 214 based on the sensed temperature and determined operation of the laser system 202 for a selected procedure.

Alternatively, or in addition to a wire provided within the housing 210, the transmission lines 300A, 300B may be traces formed into an interior wall of the housing 210 or onto the sheath 280. Nevertheless, the sensed information can be transmitted along the transmission lines 300A, 300B to a selected processing unit to determine a temperature sensed with a selected temperature sensor.

The temperature sensors 290a, 290b may, therefore, be used to determine a temperature profile that may be illustrated as an icon 292' (FIG. 3A) within the region of interest 250 relative to the device 200. At least because the temperature sensors 290a, 290b are able to sense a temperature at least a selected distance, such as the distance 232, spaced away from the surface 230, the temperature profile 292 may include a three-dimensional or two-dimensional profile or gradient of temperature(s) that is determined within a volume, such as the region of interest 250. The determined temperature profile 292 can be determined based upon a sensed temperature at a plurality of positions relative to the device 200. The plurality of sensed temperatures at the plurality of positions can then be combined to determine a 2D or 3D volume profile of temperature within the region of interest 250.

Figure 3A:
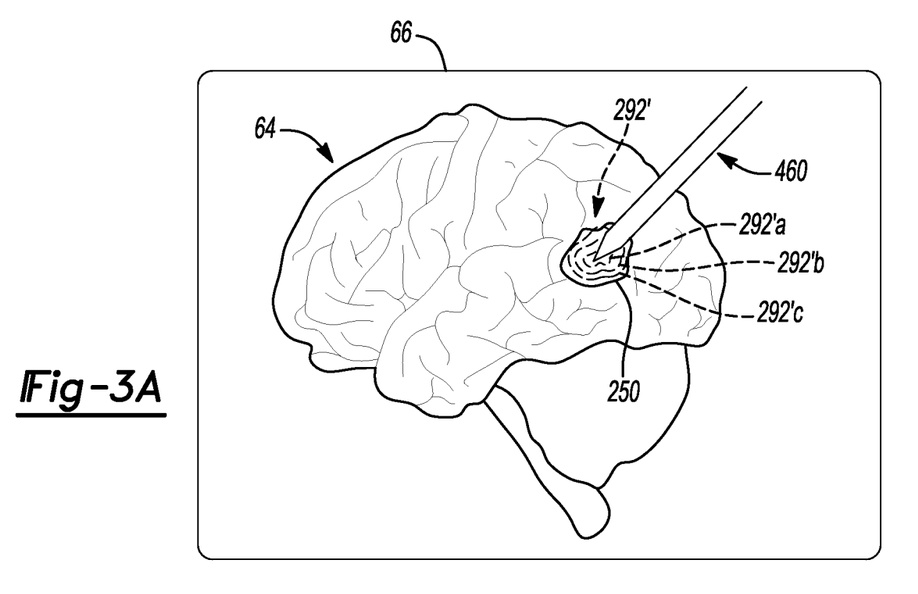
FIG. 3A is a detail view of a display device illustrating icons of an instrument and a temperature profile.

The temperature profile 292 may be used to determine if a therapy, such as a thermal therapy, is progressing as planned or has reached or achieved a planned temperature. As discussed herein, the temperature sensed by the temperature sensors 290a, 290b either alone or in combination with the determined temperature profile may be used as a part of a therapy method or method of operating the laser system 202. Further, the temperature profile may be illustrated as an icon 292' superimposed on an image of the region of interest, such as with the display 66, to illustrate the temperature profile relative to the region of interest. This is due, at least in part, to navigation of the instrument via the navigation system 10, as discussed further herein.

For example, with reference to FIGS. 1, 3 and 3A the image of the patient 64 may include an instrument icon 460 that illustrates and represents the determined position of the instrument 200. Based on one or more sensed temperatures, the temperature profile 292 may be illustrated as an icon 292' relative to the instrument and superimposed on the image 64. Further, it is understood that a temperature gradient may exist as the temperatures may vary between different positions. Thus, the temperature profile icon 292' may include gradient lines or areas. The icon may, therefore, represent a physical temperature image of the measured temperature profile. For example, as illustrated in FIG. 3A, the temperature profile icon 292' may include a first gradient area 292'a, a second gradient area 292'b, and a third gradient area 292'c. In each of the gradient areas 292'a, 292'b, and 292'c the determined temperature may be different. It is understood that more or less than three gradient areas may be shown and that the gradients need not be generally concentric but may be determined and illustrated in pockets or discrete portions relative to one another.

The temperature profile 292 may be determined and illustrated as the icon 292' at least because the temperature sensors 290a, 290b may be operated to determine a temperature at different positions at the surface 230 and distances away from the surface 232. The temperature profile may include a determination of a plurality of temperatures at or over a selected period of time, such as over ten seconds. The determined temperatures at different positions may then be illustrated as the icon 292'.

According to various embodiments, the medical device 200 can be delivered to a patient, such as to the region of interest 250, as illustrated in FIG. 3, by positioning the housing 210 at selected position and then moving the energy delivery component 214 into the housing 210. The navigation system 10 can be used to navigate the medical device 200, including either or both of the housing 210 or the energy providing component 214 to a selected position.

Figure 5:
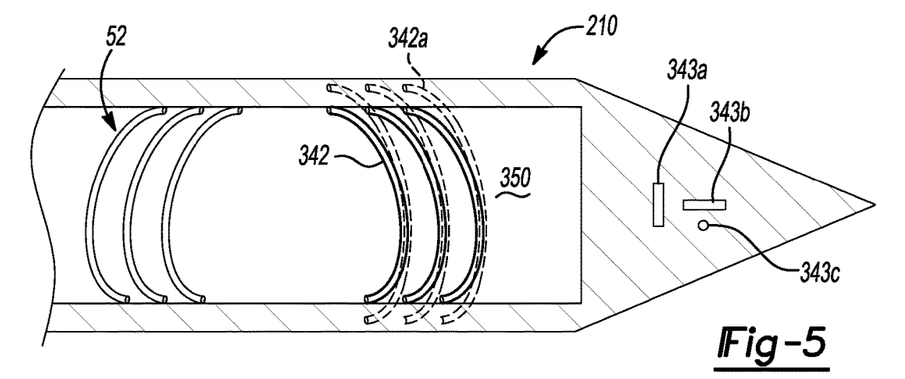
FIG. 5 is a detail cross-sectional view of a distal end of a housing of the instrument of the laser heating system.

In various embodiments the medical device tracker 52 can be formed as one or more coils of conductive material within the housing 210. With reference to FIG. 5, the tracking device 52 within the housing 210 can include one or more coils of wire or traces of conductive material 342 that are formed substantially around or on an interior surface 350 of the housing 210. It is understood that the coils of conductive material 342 may also or alternatively be formed into the housing 210, as illustrated by phantom coils 342a. The coils or wire 342 may sense or transmit an electromagnetic field that is sensed or transmitted by the localizer 42.

The tracking device, it is understood, may include a plurality of the coils 342. Further, discrete coils may be formed at angles relative to one another. Multiple angles may assist in providing multiple degrees of freedom of position (including 3 degrees x,y,z of location and 3 degrees of yaw, pitch and roll of orientation). The housing 210 can be positioned into the patient 14 using various systems such as a trajectory guide 360, as illustrated in FIG. 1. The tracking device 52 may be formed as disclosed in U.S. Pat. No. 8,644,907 issued on Feb. 4, 2014, incorporated herein by reference.

The trajectory guide 360 can include any appropriate trajectory guide such as the NAVIGUS® trajectory guide sold by Medtronic, Inc. having a place of business in Minnesota, USA. Other trajectory guides can include trajectory guides as disclosed in U.S. Patent Application Publication No. 2013/0053867 published on Feb. 20, 2013, incorporated herein by reference. The trajectory guides can assist in guiding or holding a portion of the device 200 as it is moved into the patient 14 by the user 54. The guide 360 can also be fixed at a selected position relative to the patient to allow movement of a device 200 along a selected trajectory or path into the patient 14.

Further, various individual or discrete coils, such as microcoils, can be positioned at various locations within the housing or on the housing 210. For example, detector devices 52 can include one or a plurality of microcoils 343a, 343b, 343c. The microcoils 343a-c can be positioned at various locations relative to one another such as including a common center and extending along orthogonal axes relative to one another, or may include a non-common center, but still positioned at three orthogonal axes relative to one another. It is further understood that less than three of the microcoils 343a-c may be provided and still allow for appropriate tracking of the instrument 200. Again, the microcoils 343a-c may be included within the housing 210 according to various embodiments such as an insertion into the housing or co-extrusion or molding into the housing 210. Regardless, the microcoils 343a-c may be used alone or in combination with the conductive coils 342, 342a.

Figure 6:
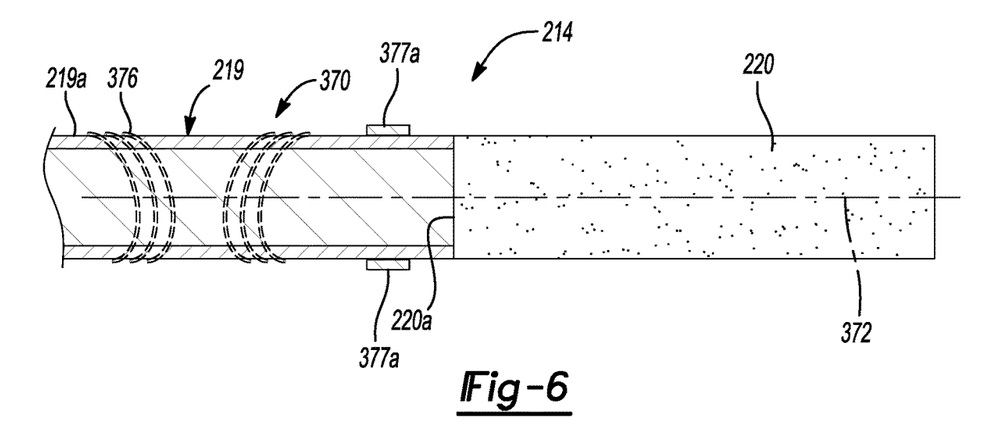
FIG. 6 is a detail cross-sectional view of a distal end of an energy delivery component of the instrument of the laser heating system.

Further, with reference to FIG. 6, the energy delivery component 214 may also include a second or separate tracking device 370. The tracking device 370 may also include one or more conductive coil elements 376 that may be formed at various angles relative to one another, such as those disclosed in U.S. Pat. No. 8,644,907 issued on Feb. 4, 2014, incorporated herein by reference. The coil elements 376 may include conductive wire wrapped around or inside of the energy transmission component 214. Alternatively, or in addition thereto, the coil elements 376 may be conductive traces formed around an outside of the energy transmission component 214.

Again the tracking device 370 can either generate or receive electromagnetic fields that are either received from or transmitted to the localizer 42. The navigation processing unit 60 can determine a position of the tracking device 370 based on the sensed fields. Further, the tracking device 370 can be provided as a plurality of tracking devices along an axial length of the energy providing component 214, such as along an axis 372. Further, the tracking device 370, even if provided as a single tracking device, can be provided at any appropriate location such as at or near the distal tip 220. The distal tip 220 may include a diffusing element that diffuses energy transmitted by the energy delivery component 214.

Accordingly, the tracking device 370 may be positioned at or just proximate of an end 220a of a diffusing element or the distal end element of the energy delivery component 214.

In addition or alternatively to the coil elements 376, microcoils 377a and 377b may be included as the second or separate tracking device 370 on the energy transmission component 214. The microcoils 377a, 377b may be positioned on an exterior surface of the energy transmission component 214 or may be incorporated into a cladding layer 219a that may surround a fiber optic portion of the energy transmission component 214. The microcoils 377a, 377b may be positioned at any appropriate location on the energy transmission component 214 similar to the conductive coils 376. Accordingly, the microcoils 377a, 377b may operate as the tracking device 370 either alone or in combination with the conductive coils 376.

By providing the tracking device 52 on the housing 210 the housing 210 can be navigated into the patient 14 such as to the tumor 250. A position of the housing 210 can be illustrated on the display device 66 such as relative to the image 64 of the patient 14, such as including an image of the brain. Further, the tracking device 370 can allow for determining and navigating the energy delivery component 214 relative to the patient 14, as well. Therefore the housing 210 may be positioned within the patient prior to positioning the energy delivery component 214 in the patient 14, however, the position of the energy delivery component 214 can be separately known or determined based upon tracking the tracking device 370 and the navigation processing unit determining the position. In this way the housing 210 can be positioned into the patient 14 at a first selected time and the image delivery component 214 can be positioned in the patient 14 at a second time, different, such as after, the positioning of the housing 210, while still allowing a determination of a position over the image delivery component.

Positioning of the distal end 220 of the energy delivery component 214 can assist in providing an efficient and discrete therapy to the patient 14. For example, as noted above, delivering thermal energy to the patient 14 may be provided by transmitting energy, such as laser energy, with the energy delivery component 214. The laser energy may be delivered diffusely through the distal tip 220, such as with a diffusion element (e.g., a diffusion element as disclosed in U.S. Patent Application Publication No. 2012/0245573, incorporated herein by reference). Therefore the position of the distal end 220 may be selected to be substantially, discretely, and precisely positioned within the patient 14.

Further, during a time of therapy it may be selected to move the distal end 220 of the energy delivery component 214 without moving the housing 210. For example, the distal end 220 of the energy delivery component 214 may be moved along the length or along an axis 211 of the housing 210 to different axial positions within the housing 210. Moving the energy delivery component 214 may provide the energy, such as thermal energy, to different locations along the housing 210. Therefore, tracking energy delivery component 214 separate from a position of the housing 210 can assist in determining, substantially, precisely, (such as within about 0.1 mm to about 1 mm) the position of the distal end 220 for continuing or altering therapy to the patient 14.

Figure 7:
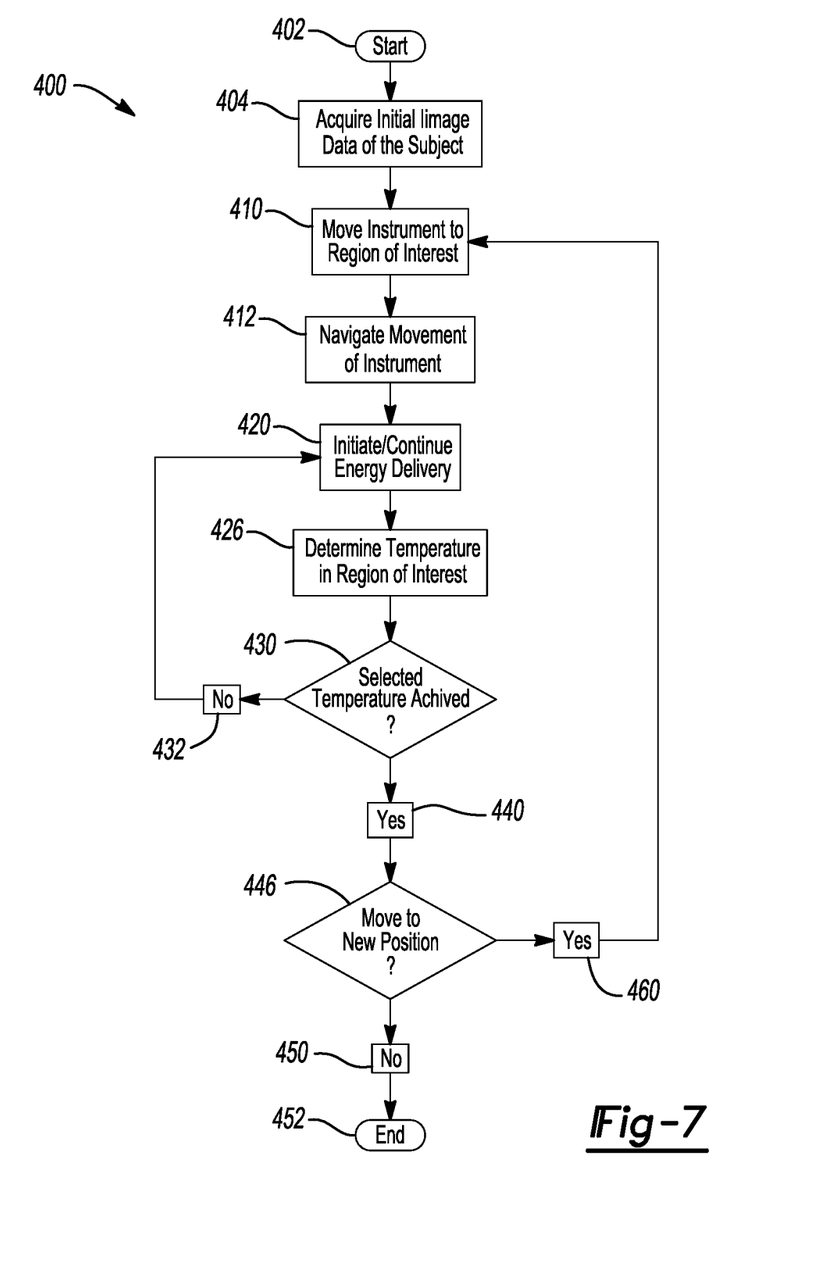
FIG. 7 is a flowchart illustrating operation of an energy delivery system.

With reference to FIG. 7, the laser system 202 can be operated to perform a selected procedure, as illustrated in flowchart 400. Generally, the procedure can start in a start block 402. The procedure may then include acquiring initial image data of the subject in block 404. The initial image data may include MRI image data, such as acquired with the imaging system 12, and displayed on the display 66. The initial image data may be used to plan a procedure, such as determining a location of the region of interest 250 and selecting a trajectory and selected positions for positioning the instruments 200 and/or the distal end 220 of the energy delivered component 214.

After determining or selecting a plan, user 54 or other appropriate instrumentation such as a robotics system, may move the instrument to the region of interest in block 410. While the instrument is moved, the instrument may be navigated in block 412. As discussed above, navigation of the instrument may include navigation of an entire portion of the instrument 200, or selected portions thereof. For example, the housing 210 may be navigated separately from the energy delivery component 214. Nevertheless, the instrument can be moved to the region of interest in block 410 via the navigation block 412.

Once the instrument is at the region of interest, initiation (or continuation) of energy delivery occurs in block 420. As discussed above, the delivery of energy may increase the temperature in the region of interest 250. Therefore, determination of the temperature and or temperature profile of the region of interest in block 426 may occur. The determination of the temperature in the region of interest 426 can be based upon the sensed temperature, such as with the temperature sensor components 290a, 290b. Further, as discussed above, the temperature may be sensed at the varied positions within the region of interest 250, including along a length of the instruments 200 and at a distance away from the surface 230 of the housing 210.

After determining the temperature in the region of interest in block 426, a determination of whether a selected temperature is achieved occurs in block 430. The determination may be made by evaluating the determined temperature and/or temperature profile form block 426. For example, a user may view the icon 292' and determine if the illustrated temperature is the selected temperature. Alternatively, or in addition thereto, one or more of the processing units may compare the determined temperature from block 426 to a planned temperature that may be determined prior to the procedure and stored in the memory 62. The processing unit may then recall the planned temperature and/or temperature profile and compare it to the determined temperature in 426 and automatically determine if the selected temperature have been achieved.

If a selected temperature is not achieved in block 430, a "no" block 432 may be followed to continue energy delivery in block 420. Therefore, energy delivery can be initiated and continued in block 420 until the determined temperature in block 426 is determined to be the selected in block 430. The temperature determination in block 426 may be substantially real time, such as determined every 0.1 seconds to about 30 seconds, or other appropriate frequency. Thus, the determination of whether the selected temperature is achieved in block 430 may be performed at the same frequency.

Once the selected temperature is determined to be achieved in block 430, a "yes" block 440 may be followed to determine whether to move the device to a new position in block 446. If it is determined to not move the instrument 200 to a new position, a "no" path 450 may be followed and the procedure may end in end block 452. Ending the procedure in block 452 can include confirming that a selected tissue has been killed in the region of interest 250, closing a burr hole in the patient 14, and other appropriate procedures based upon a selected procedure being performed with the device 200.

If it is determined in block 446 to move the device 200 to a new position, a "yes" block 460 may be followed to block 410 to move an instrument to a region of interest which may be determined than a first region of interest or may be within the region of interest at a second position. The initiation of delivery of energy in block 420 can then be reinitiated at the new position and the method 400 may then be followed as discussed above.

As discussed above, movement of the device 200 to a new position in block 446 can include moving the entire device 200 or only moving the energy delivery component 214 to a different position within the housing 210. Again, due to the tracking devices 52, 370, the housing 210 can be navigated separately from the energy delivery component 214. Furthermore, icons can be superimposed on the image 64, including an icon 460 (illustrated in FIG. 1) to illustrate a position of the instrument 200, or portions thereof including the housing 210 or the energy delivery component 214, for viewing by the user 54. As discussed above, the patient space and image space may be registered to allow for the illustration of the icon 460 at the correct position. The user 54 can therefore navigate and view the location of the device 200 relative to the image 64 to determine whether a plan is being followed, a location of the device 200 is being achieved, and other position information regarding the device 200 relative to the patient 14.

It is understood that the method illustrated in the flowchart may include portions executed by one or more of the processing units discussed above. For example, determination of a temperature in a region of interest in block 426 may be performed by receiving a signal from the temperature sensors 290a, 290b and calculating the temperature based on the signal. Further, thermal energy may be ceased or the method may be ended automatically if the determination in block 430 is to follow the "yes" block 440. Thus, automatic shut-off of the laser system 202 may occur to assist in more closely following a plan or assisting in assuring that only a selected temperature is reached.

The temperature sensors 290a, 290b also allow for a real time determination of a temperature in the region of interest. As the temperature sensors are at the region of interest 250, the signals received are based on the current (e.g., within a reaction and transmission time of the selected temperature sensor component device, including within 1 second or less) temperature in the region of interest 250. Thus, the thermal therapy may be delivered accurately and with tight controls. Further, the temperature sensors 290a, 290b eliminate the need for an external device to measure or determine the temperature of the selected region, such as using MRI data.

Accordingly, the navigation system 10 and the temperature sensors 290a, 290b allow the device 200 to be positioned relative to the patient 14 without requiring continuous or intermittent imaging of the patient 14 during the procedure. The temperature sensors 290a, 290b are used to sense the temperature within the region of interest 250 to determine whether a selected temperature has been achieved. Achieving a selected temperature may allow a therapeutic result on the patient 14. Further, the navigation system 10 can be used to navigate the instrument 200 to a selected position within the patient 14 without using the imaging device 12 to image the patient 14 during or after movement of the device 200. Therefore, the imaging device 12 can be used to acquire image data of the patient 14 prior to positioning the instrument 200 within the patient 14 and performing a thermal energy treatment on the patient 14. The imaging device 12 may not be necessary during any other portion of the procedure to provide thermal energy to the patient 14 with the device 200. Thus, the imaging system 12 may only be required to acquire initial image data for planning and navigation and not for performing movement or thermal therapy on the patient 14.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to measure temperature in a region of interest, comprising:
    an instrument including:
        an exterior housing have an external wall defining an internal blind bore extending a first length from a first housing end to a second housing end and configured to be moved to a position within a volume,
        an energy delivery component extending a second length from a first energy delivery component end to a second energy delivery component end and configured to be moved to a position within the volume and deliver energy to affect a thermal therapy at a region of interest within the volume outside of the exterior housing;
    a first indirect temperature sensor embedded within the external wall of the exterior housing and adjacent the first energy delivery component end to sense a temperature within the region of interest, wherein in the region of interest is a distance spaced away from an external surface of the housing and wherein the external wall entirely surrounds the first indirect temperature sensor;
    a second contact temperature sensor separate from and spaced away from the first indirect temperature sensor and fixed within the external wall of the exterior housing, wherein the second contact temperature sensor is positioned and configured to sense a temperature adjacent to the external surface of the exterior housing; and
    a tracking device fixed to the instrument;
    an energy source configured to deliver energy through the energy delivery component to affect the thermal therapy in the region of interest;
    a processor configured to execute instructions to:
        determine a temperature profile within the region of interest based on a signal from both the first indirect temperature sensor and the second contact temperature sensor, and determine a position of the instrument within the region of interest;

wherein the thermal therapy is operable to increase a temperature in the region of interest.

2. The system of claim 1, wherein the first indirect temperature sensor includes an ultrasound temperature sensor.

3. The system of claim 1, wherein the processor is further configured to execute instructions to stop delivery of energy when the temperature profile reaches a selected temperature.

4. The system of claim 1, further comprising:
a display to display an image representing the region of interest and an icon representing the determined position of at least a portion of the instrument.

5. The system of claim 4, wherein the display is further configured to display a temperature icon to represent the determined temperature profile including a representation of a physical temperature image of the measured temperature profile.

6. A system to measure temperature in a region of interest, comprising:
an instrument extending a length from a first end to a second end and configured to be moved to a position within a volume and deliver a laser light to provide a thermal therapy to a region of interest within the volume, the instrument having an exterior housing and an energy delivery component positioned in a bore defined by an external wall of the exterior housing;
an indirect temperature sensor embedded within and surrounded by the external wall of the exterior housing, wherein the indirect temperature sensor is between an external surface and an internal surface of the external wall of the exterior housing to sense a temperature within the region of interest, wherein the region of the interest is at a distance spaced away from the external surface of the exterior housing;
an energy source configured to deliver energy through the instrument to affect the thermal therapy in the region of interest;
a tracking device fixed to the instrument to track a position of the instrument;
a processor configured to execute instructions to determine a temperature profile of the region of interest relative to the instrument within the region of interest based upon both the sensed temperature from the indirect temperature sensor and a determined position of the instrument;
wherein the thermal therapy is operable to increase a temperature in the region of interest.

7. The system of claim 6, further comprising:
a navigation processor configured to determine the position the tracking device; and
a display device configured to display an image representing the region of interest superimposed with an icon representing the determined position of the instrument.

8. The system of claim 6, wherein the indirect temperature sensor includes a plurality of indirect temperature sensors.

9. The system of claim 8, wherein the plurality of indirect temperature sensors are spaced along at least a portion of the length of the instrument.

10. The system of claim 9, further comprising a direct temperature sensor configured to measure the temperature of the region of interest at the external surface of the instrument.

11. A method to measure temperature in a region of interest, comprising:
tracking a position of an instrument having an exterior housing relative to the region of interest;
directing laser light energy through an emitting portion of an energy delivery component within the exterior housing to heat the region of interest;
receiving a temperature signal from an indirect temperature sensor that is embedded in an external wall of the exterior housing, wherein the external wall forms a structure that surrounds the indirect temperature sensor;
determine a position of the instrument;
determining a temperature at the determined position relative to the region of interest with the received temperature signal from the indirect temperature sensor by operating the indirect temperature sensor to sense a temperature a distance away from the exterior housing;
determining when a selected temperature in the region of interest is achieved by evaluating the received temperature signal from the indirect temperature sensor and the determined position of the instrument; and
ceasing the heating of the region of the region of interest when the selected temperature is determined to be achieved.

12. The method of claim 11, further comprising:
tracking the energy delivery component during movement of the energy delivery component into the region of interest.

13. The method of claim 12, further comprising:
displaying an icon representing a position of the energy delivery component based on the tracking of the energy delivery component.

14. The method of claim 11, further comprising:
operating the indirect temperature sensor to sense a temperature a distance from the energy delivery component.

15. The method of claim 14, further comprising:
operating a processor to determine a temperature profile relative to the energy delivery component.

16. The method of claim 15, further comprising:
viewing a display of a temperature icon representing the determined temperature profile.

* * * * *